US011231416B2

(12) United States Patent
Tavernier et al.

(10) Patent No.: US 11,231,416 B2
(45) Date of Patent: *Jan. 25, 2022

(54) VIRUS-LIKE PARTICLE (VLP) BASED SMALL MOLECULE-PROTEIN INTERACTION TRAP

(71) Applicants: VIB VZW, Ghent (BE); Universiteit Gent, Ghent (BE)

(72) Inventors: Jan Tavernier, Balegem (BE); Sven Eyckerman, Nazareth (BE)

(73) Assignees: VIB VZW, Ghent (NL); Universiteit Gent, Ghent (NL)

(*) Notice: Subject to any disclaimer, the term of this patent is extended or adjusted under 35 U.S.C. 154(b) by 0 days.

This patent is subject to a terminal disclaimer.

(21) Appl. No.: 16/865,780

(22) Filed: May 4, 2020

(65) Prior Publication Data
US 2020/0278345 A1 Sep. 3, 2020

Related U.S. Application Data

(63) Continuation of application No. 16/532,154, filed on Aug. 5, 2019, now Pat. No. 10,641,765, which is a continuation of application No. 15/559,748, filed as application No. PCT/EP2016/056331 on Mar. 23, 2016, now Pat. No. 10,379,115.

(30) Foreign Application Priority Data

Mar. 23, 2015 (GB) ..................... 1504859

(51) Int. Cl.
| | |
|---|---|
| *C07K 14/705* | (2006.01) |
| *A61K 38/17* | (2006.01) |
| *A61K 38/00* | (2006.01) |
| *A61K 9/00* | (2006.01) |
| *A61P 35/00* | (2006.01) |
| *G01N 33/543* | (2006.01) |
| *G01N 33/68* | (2006.01) |
| *C07K 14/005* | (2006.01) |
| *C12N 7/00* | (2006.01) |
| *C12N 9/06* | (2006.01) |

(52) U.S. Cl.
CPC ....... *G01N 33/5436* (2013.01); *C07K 14/005* (2013.01); *C12N 7/00* (2013.01); *C12N 9/003* (2013.01); *G01N 33/54313* (2013.01); *G01N 33/54353* (2013.01); *G01N 33/6803* (2013.01); *G01N 33/6845* (2013.01); *G01N 33/6848* (2013.01); *C07K 2319/43* (2013.01); *C07K 2319/735* (2013.01); *C12N 2740/16023* (2013.01); *C12N 2740/16042* (2013.01); *C12N 2740/16222* (2013.01); *G01N 2333/161* (2013.01); *G01N 2333/90666* (2013.01)

(58) Field of Classification Search
CPC ............... C07K 2319/43; A61K 38/00; A61K 38/1774; A61K 39/0011; A61K 39/001104

See application file for complete search history.

(56) References Cited

U.S. PATENT DOCUMENTS

| | | | |
|---|---|---|---|
| 7,235,629 B2 | 6/2007 | Eyckerman et al. |
| 7,291,458 B2 | 11/2007 | Broekaert et al. |
| 7,423,113 B2 | 9/2008 | Tavernier et al. |
| 7,575,878 B2 | 8/2009 | Tavernier et al. |
| 7,855,270 B2 | 12/2010 | Eyckerman et al. |
| 8,003,757 B2 | 8/2011 | Eyckerman et al. |
| 8,048,986 B2 | 11/2011 | Eyckerman et al. |
| 2004/0166538 A1 | 8/2004 | Eyckerman et al. |
| 2014/0030746 A1 | 1/2014 | Tavernier et al. |
| 2014/0348789 A1 | 11/2014 | Tavernier et al. |
| 2015/0011417 A1 | 1/2015 | Tavernier et al. |
| 2015/0153355 A1 | 6/2015 | Tavernier et al. |

FOREIGN PATENT DOCUMENTS

| | | |
|---|---|---|
| WO | 9002809 A1 | 3/1990 |
| WO | 9220791 A1 | 11/1992 |
| WO | 9710330 A1 | 3/1997 |
| WO | 9732017 A1 | 9/1997 |
| WO | 0102551 A2 | 1/2001 |
| WO | 0190188 A2 | 11/2001 |
| WO | 2011057134 A1 | 5/2011 |
| WO | 2012117031 A1 | 9/2012 |
| WO | 2013174999 A1 | 11/2013 |
| WO | 2016150992 A1 | 9/2016 |

OTHER PUBLICATIONS

Baker, D.J., et al. "The Binding of Trimethoprim to Bacterial Dihydrofolate Reductase." FEBS Letters, vol. 126, No. 1, 1981, pp. 49-52.
Caligiuri, Maureen, et al. "MASPIT: Three-Hybrid Trap for Quantitative Proteome Fingerprinting of Small Molecule-Protein Interactions in Mammalian Cells." Chemistry Biology, vol. 13, No. 7, 2006, pp. 711-722.
De Felipe, Karim Suwwan, et al. "Correlation between Ligand-Receptor Affinity and the Transcription Readout in a Yeast Three-Hybrid System." Biochemistry, vol. 43, No. 32, 2004, pp. 10353-10363.
Eyckerman et al., Trapping mammalian protein complexes in viral particles, Nature Communication, Apr. 28, 2016, pp. 11416, vol. 7.
Gallagher, Sarah S, et al. "An Orthogonal Dexamethasone-Trimethoprim Yeast Three-Hybrid System." Analytical Biochemistry, vol. 363, No. 1, 2007, pp. 160-162.

(Continued)

*Primary Examiner* — Barry A Chestnut
(74) *Attorney, Agent, or Firm* — Patent Law Works, LLP

(57) ABSTRACT

This disclosure relates to a virus-like particle in which a small molecule-protein complex is entrapped, ensuring the formation of the small molecule-protein complex under physiological conditions, while protecting the small molecule-protein complex during purification and identification. The disclosure further relates to the use of such virus-like particle for the isolation and identification of small molecule-protein complexes.

9 Claims, 3 Drawing Sheets
Specification includes a Sequence Listing.

(56) References Cited

OTHER PUBLICATIONS

Licitra, Edward et al., "A Three-Hybrid System for Detecting Small Ligand-Protein Receptor?Interactions." Proceedings of the National Academy of Sciences of the United States of America, vol. 93, No. 23, 1996, pp. 12817-12821.

Lin, Hening, et al. "Dexamethasone-Methotrexate: An Efficient Chemical Inducer of Protein Dimerization In Vivo." Journal of the American Chemical Society, vol. 122, No. 17, 2000, pp. 4247-4248.

PCT International Search Report and Written Opinion, Application No. PCT/EP2016/056331, dated May 30, 2016, 9 pages.

MTX-PEG6-tamoxifen

MTX-PEG6-reversine

MTX-PEG6-simvastatin

VIRUS-LIKE PARTICLE (VLP) BASED SMALL MOLECULE-PROTEIN INTERACTION TRAP

CROSS-REFERENCE TO RELATED APPLICATIONS

This application is a continuation of and claims priority to U.S. application Ser. No. 16/532,154, filed Aug. 5, 2019, pending, which is a continuation to U.S. application Ser. No. 15/559,748, filed Sep. 19, 2017, issued, which is a national phase entry under 35 U.S.C. § 371 of International Patent Application PCT/EP2016/056331, filed Mar. 23, 2016, designating the United States of America and published in English as International Patent Publication WO 2016/150992 A1 on Sep. 29, 2016, which claims the benefit under Article 8 of the Patent Cooperation Treaty to Great Britain Patent Application Serial No. 1504859.8, filed Mar. 23, 2015, the disclosure of each of which is hereby incorporated herein in its entirety by this reference.

TECHNICAL FIELD

The present application relates to a virus-like particle, in which a small molecule-protein complex is entrapped, ensuring the formation of the small molecule-protein complex under physiological conditions, while protecting the small molecule-protein complex during purification and identification. The application further relates to the use of such virus-like particle for the isolation and identification of small molecule-protein complexes.

STATEMENT ACCORDING TO 37 C.F.R. § 1.821(c) or (e)—SEQUENCE LISTING SUBMITTED AS A TXT FILE

Pursuant to 37 C.F.R. § 1.821(c) or (e), files containing a TXT version of the Sequence Listing have been submitted concomitant with this application, the contents of which are hereby incorporated by reference.

BACKGROUND

Molecular interactions, such as protein-protein interactions, are essential components of virtually all cellular processes. The binding of two or more compounds in a cell can have a wide array of effects, including modulating signal transduction, regulating gene transcription, and promoting cellular replication or apoptosis. Several human diseases are associated with malfunctioning of molecular interactions.

Researchers have developed several approaches in attempts to identify molecular interactions. A major breakthrough in the detection of protein-protein interactions was obtained by the introduction of the genetic approaches, of which the yeast two-hybrid (Fields and Song, 1989) is the most important one. Although this technique became widely used, it has several drawbacks. The fusion proteins need to be translocated to the nucleus, which is not always evident. Proteins with intrinsic transcription activation properties may cause false positive signals. Moreover, interactions that are dependent upon secondary modifications of the protein such as phosphorylation cannot be easily detected.

Several alternative systems have been developed to solve one or more of these problems.

Approaches based on phage display do avoid the nuclear translocation. WO9002809 describes how a binding protein can be displayed on the surface of a phage, such as a filamentous phage, wherein the DNA sequence encoding the binding protein is packaged inside the phage. Phages, which bear the binding protein that recognizes the target molecule, are isolated and amplified. Several improvements of the phage display approach have been proposed, as described, e.g., in WO9220791, WO9710330 and WO9732017.

However, all these methods suffer from the difficulties that are inherent to the phage display methodology: the proteins need to be exposed at the phage surface and are so exposed to an environment that is not physiological relevant. Moreover, when screening a phage library, there will be a competition between the phages that results in a selection of the high affinity binders.

A major improvement in the detection of protein-protein interactions was disclosed in WO0190188, describing the so called Mappit system. The method, based on a cytokine receptor, allows not only a reliable detection of protein-protein interactions in mammalian cells, but also modification-dependent protein interactions can be detected, as well as complex three hybrid protein-protein interactions mediated by a small compound (Caligiuri et al., 2006). However, although very useful, the system is limited in sensitivity and some weak interactions cannot be detected. Moreover, as this is a membrane-based system, nuclear interactions are normally not detected. Recently, a cytoplasmic interaction trap has been described, solving several of those shortcomings (WO2012117031). However, all these "genetic" systems rely on the overexpression of both interaction partners, which may result in false positive signals, due to the artificial increase in concentration of the interaction partners.

As an alternative for the genetic protein-protein interaction detection methods described above, biochemical or co-purification strategies combined with mass spectrometry (MS)-based proteomics (Paul et al., 2011; Gingras et al., 2007) can be used. For the co-purification strategies, a cell homogenate is typically prepared by a detergent-based lysis protocol, followed by capture using a (dual) tag approach (Gavin et al., 2002) or via specific antibodies (Malovannaya et al., 2011). The protein complex extracted from the "soup" of cell constituents must then survive several washing steps, mostly to compensate for the sensitivity of contemporary MS instruments, before the actual analysis occurs. There are no clear guidelines on the extent of washing or on available buffers and their stringency. Most lysis and washing protocols are purely empirical in nature and were optimized using model interactions. It is, therefore, hard to speculate on the loss of factors during these steps (false negatives), or the possibility of false interactions due to loss of cellular integrity (false positives). Use of metabolic labeling strategies allows separation between the proteins sticking to the purification matrix, and between the proteins that associate specifically to the bait protein. Depending on the purification conditions and the sensitivity of the MS instruments used, it is no exception to find more than 1000 proteins in the eluted fraction of a gel-free AP-MS experiment (www.crapome.org).

The classical approach to identify target proteins for small molecules relies on the use of "purification handles" that are added to the small molecule. A biotin group is typically used to modify the small molecule, preferentially through a linker and on a permissive site of the molecule. The modified small molecule is then used to capture the associated molecules by a classical pull-down approach using streptavidin beads on a lysate. In a recent implementation, Ong and colleagues describe the use of quantitative proteomics based on metabolic labeling (Stable Isotope Labeling of Amino acids in Cell Culture—SILAC), to define the proteins that bind specifically to a small molecule. The authors use "small-molecule beads" that were prepared by direct chemical coupling of the small molecules to the beads (Ong et al., 2009). Bantscheff and colleagues described a method wherein a panel of broad range kinase inhibitors was coupled to a matrix. This matrix was then incubated with cell lysates to bind a significant portion of the kinome. By adding increasing concentration of candidate kinase inhibitors, on- and off-target kinases can be identified (Bantscheff et al., 2007). A major limitation of this approach is the lack of broad specificity inhibitors outside of the kinase family making it difficult to translate the strategy to other protein target families. In addition, off-targets outside of the kinase family are not readily identified. Another very recent development is thermal profiling to assess the change in thermal stability of proteins upon binding of a small molecule. Proteins tend to aggregate depending on the temperature which is affected by binding of ligands or posttranslational modifications. Savitski and colleagues performed this analysis in a proteome-wide manner using quantitative proteomic approaches and were able to identify known and novel targets for different small molecules (Savitski et al., 2014).

Recently, a co-purification technique has been disclosed in WO2013174999 that allows for evaluating protein-protein interactions in their physiological environment. The complexes are trapped via the p55 GAG protein into artificial virus-like particles (VLPs) that are budded from human cells. The complexes are protected during the enrichment process in a so-called "Virotrap particle." However, Virotrap, even in its conditional mode of operation, does not identify previously unknown small molecule-protein interactions.

It would be advantageous to entrap small molecule-protein complexes under physiological conditions and thereby evaluate physiologically relevant small molecule-protein interactions.

BRIEF SUMMARY

To evaluate whether a solution could be found for isolating previously unidentified small molecule-protein interactions under physiologically relevant conditions, different isolation protocols were evaluated.

Surprisingly, it was found that new methods derived from the recently described Virotrap protocol (WO2013174999) also can be used to trap a small molecule together with its physiological binding partners into VLPs that are budded from human cells. The very mild enrichment of the complex ensures the identification of relevant small molecule-protein interactions in physiological environments.

According to a first aspect, provided herein are artificial virus-like particles (VLPs), comprising:
(a) a VLP-forming polypeptide;
(b) a fusion construct comprising two small molecules covalently linked to each other, wherein the first small molecule interacts with the VLP-forming polypeptide and the second small molecule interacts with at least one polypeptide different from the VLP-forming polypeptide; and
(c) a polypeptide interacting with the second small molecule of (b).

According to particular embodiments, the VLP-forming polypeptide is a fusion protein. According to further particular embodiments, the VLP-forming polypeptide is a fusion protein comprising the HIV p55 GAG protein.

Also provided is the use of an artificial VLP for the detection of small molecule-protein interactions.

According to a further aspect, methods are provided for detecting small molecule-protein interactions, comprising:
(1) expressing a VLP-forming polypeptide in a cell;
(2) recruiting a fusion construct comprising two small molecules covalently linked to each other, wherein the first small molecule interacts with the VLP-forming polypeptide and the second small molecule interacts with at least one polypeptide different from the VLP-forming polypeptide, to the VLP-forming polypeptide;
(3) allowing a polypeptide to interact with the second small molecule of (2);
(4) isolating the VLPs; and
(5) analyzing the entrapped complex.

According to particular embodiments, the VLPs are isolated by an affinity chromatography-based method.

According to specific embodiments, the entrapped complex is analyzed using a mass spectrometry-based method.

DETAILED DESCRIPTION

Definitions

Figure 1:
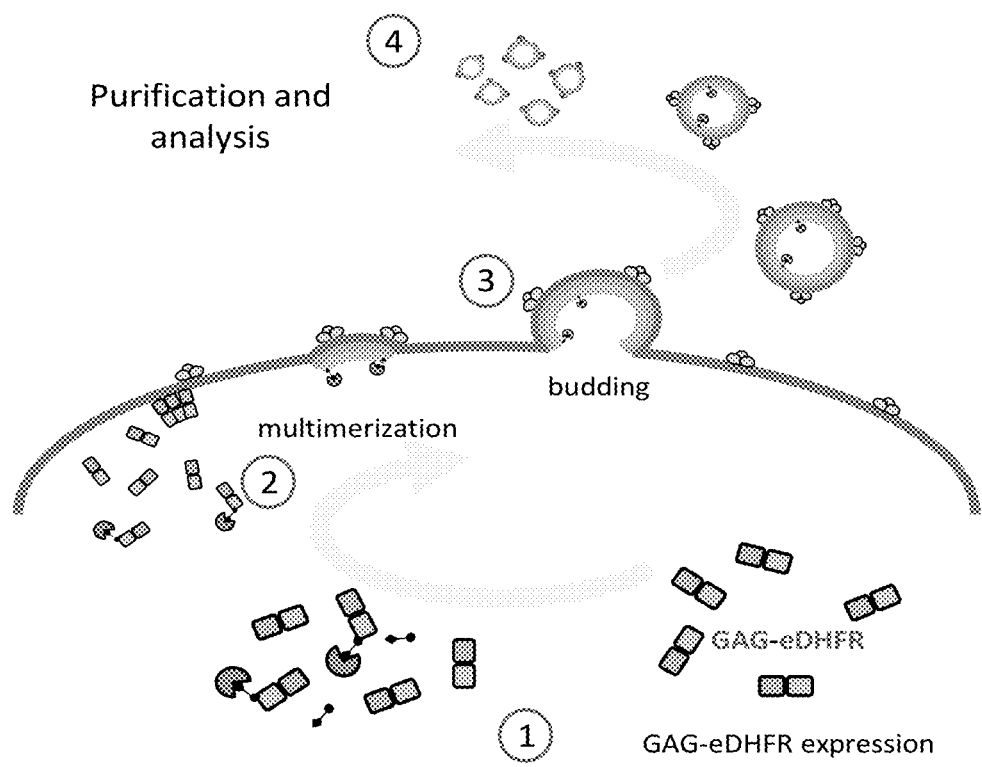
FIG. 1: General overview of the small molecule-protein trapping method. Expression of a GAG-eDHFR fusion protein (1) (i.e., the VLP-forming polypeptide) results in submembrane multimerization (2) and subsequent budding of virus-like particles (VLPs) from cells (3). The VLPs can then be purified and analyzed by co-complex MS analysis (4) providing a way of purifying protein complexes under physiological conditions. The addition of a small molecule fusion construct during VLP production results in binding of the small molecule fusion construct to the GAG-eDHFR fusion protein and to trapping of small molecule-interacting proteins in the VLPs.
Figure 2:
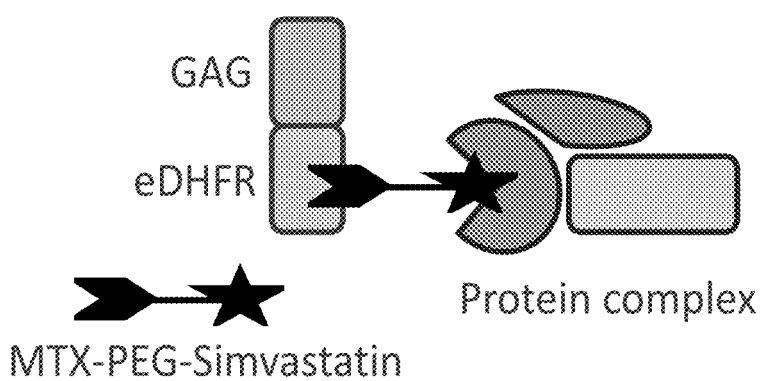
FIG. 2: Scheme for the use of the VLP-forming polypeptide GAG-eDHFR to trap small molecule-protein interactions. As a non-limiting example, a target interacting protein complex is recruited to the GAG-eDHFR fusion protein via the small molecule fusion construct methotrexate (MTX)-PEG-simvastatin.
Figure 3:
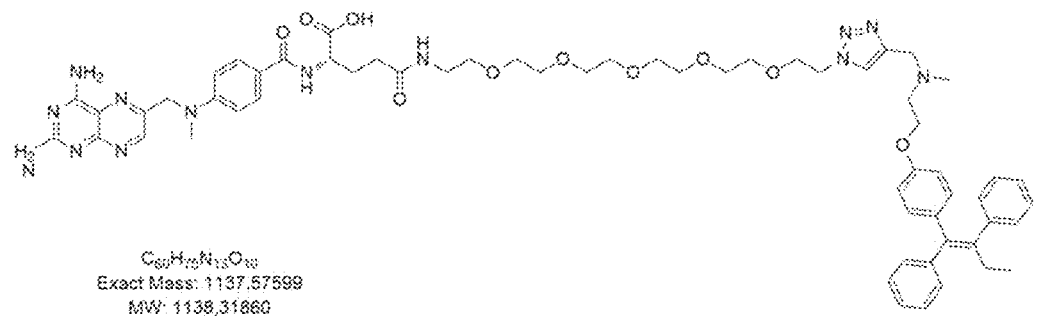
FIG. 3: Chemical structures of the different small molecule fusion constructs used in this study.
Figure 3:
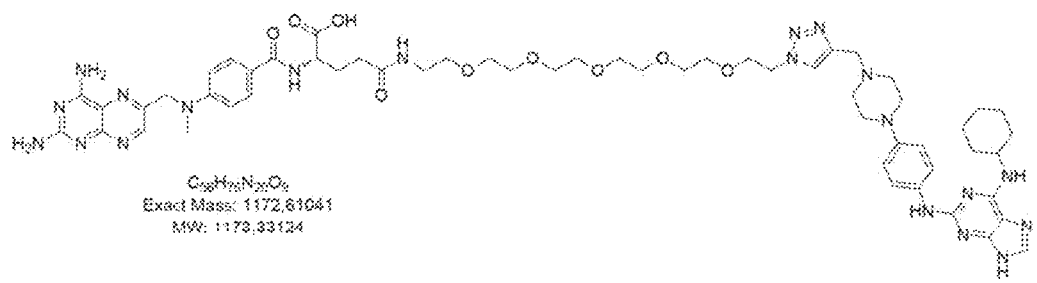
Figure 3:
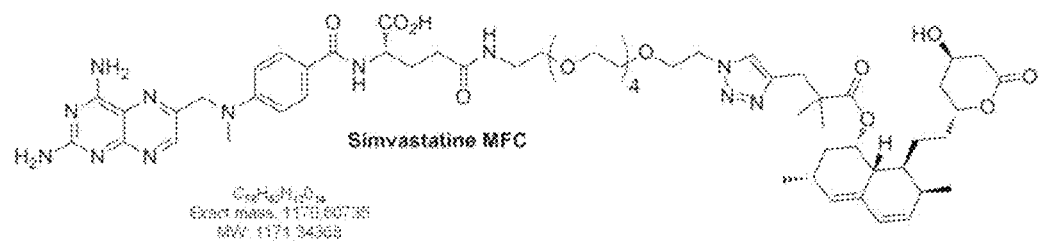

This disclosure will be described with respect to particular embodiments and with reference to certain drawings but the disclosure is not limited thereto, but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

The following terms or definitions are provided solely to aid in the understanding of the disclosure. Unless specifically defined herein, all terms used herein have the same meaning as they would to one skilled in the art of this disclosure. Practitioners are particularly directed to Sambrook et al., *Molecular Cloning: A Laboratory Manual*, 2nd ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. The definitions provided herein should not be construed to have a scope less than understood by a person of ordinary skill in the art.

A "virus-like particle," or "VLP," as used here, is a particle comprising at least a viral particle-forming polypeptide, but preferably without the viral DNA or RNA. "Virus-like particle-forming polypeptides" or "VLP-forming polypeptides," as used here, are known to the person skilled in the art and are polypeptides or proteins that allow the assembly of viral particles, and preferably budding of the particles of the cell. A VLP-forming protein is sufficient to form a VLP, and there will typically be more than one (typically identical) VLP-forming protein in a VLP. According to specific embodiments, the VLP-forming polypeptides are fusion proteins of a VLP-forming protein and another protein, polypeptide or protein subunit.

It is particularly envisaged that the VLPs as described herein do not contain viral genetic material, so they are non-infectious.

"Polypeptide" refers to a polymer of amino acids and does not refer to a specific length of the molecule. This term also includes modifications of the polypeptide, such as glycosylation, phosphorylation and acetylation of the naturally occurring amino acids, and includes substitutions of one or more of the naturally occurring amino acids with non-natural analogs.

The "fusion construct comprising two small molecules" as used herein comprises two small molecules covalently linked to each other, wherein the first small molecule functions as and is referred to as "recruiting element" that interacts with the VLP-forming polypeptide. The second small molecule functions as and is referred to as "bait" and interacts with at least one polypeptide different from the virus-like particle-forming polypeptide (the "prey" polypeptide).

"Small molecules" are low molecular weight organic compounds, having a molecular weight of 10,000 Daltons or less, of natural or synthetic nature.

"Interacts with" typically means, but is not limited to, "binds to." Of note, interaction can be indirect as well.

The term "recruited to" in relation to the fusion construct that is recruited to the VLP refers to allowing the recruiting element of the fusion construct to interact with and/or bind to the VLP-forming polypeptide.

According to a first aspect, an artificial virus-like particle (VLP) is provided, comprising:
  (a) a VLP-forming polypeptide;
  (b) a fusion construct comprising two small molecules covalently linked to each other, wherein the first small molecule ("recruiting element") interacts with the VLP-forming polypeptide and the second small molecule ("bait") interacts with at least one polypeptide different from the VLP-forming polypeptide; and
  (c) a polypeptide ("prey") interacting with the second small molecule ("bait") of (b).

The VLPs can be derived from numerous viruses. Examples of such particles have been described in the art and include, but are not limited to particles derived from virus families including Parvoviridae (such as adeno-associated virus), Retroviridae (such as HIV), Flaviviridae (such as Hepatitis C virus), Orthomyxoviridae (such as Influenza virus), and Rhabdoviridae (such as vesicular stomatitis virus). The particles typically comprise viral structural proteins, such as Envelope or Capsid, and result in the self-assembly of virus-like particles.

According to specific embodiments, the VLP-forming polypeptide is a fusion protein. Thus, according to these embodiments, rather than taking a viral structural protein as such, the protein (or a functional part thereof) is fused to another polypeptide. As such, the viral particle-forming polypeptide then comprises (or consists of) two different polypeptide domains, typically (but not necessarily) taken from two different proteins.

According to particular embodiments, the VLP-forming polypeptide may be a modified form of the natural occurring VLP-forming protein, as long as the modifications do not inhibit the particle formation. A modification or functional fragment as used here is a modification or functional fragment that is still capable of forming virus-like particles that are capable of entrapping the small molecule-protein complex according to the disclosure. Examples of modifications include, e.g., deletions and/or mutations. Particularly envisaged are deletions and/or mutations that reduce the binding of the VLP-forming polypeptide with host proteins with the objective to minimize the background protein list.

A particularly envisaged VLP-forming polypeptide is the HIV p55 GAG protein. According to further particular embodiments, the VLP-forming polypeptide is a fusion protein comprising the HIV p55 GAG protein. Preferably, the polypeptide fused to the p55 GAG protein comprises dihydrofolate reductase (DHFR), even more preferably, *E. coli* dihydrofolate reductase (eDHFR).

The artificial VLP contains a fusion construct comprising two small molecules covalently linked to each other. The two small molecules typically are independently selected from compounds with a molecular weight of 10,000 Daltons or less. Particularly, the fusion construct comprises two compounds with each a molecular weight of 5,000 Daltons or less. Particularly, the small molecule comprises compounds with a molecular weight of 2,000 Daltons or less. Particularly, the small molecule comprises compounds with a molecular weight of 1,000 Daltons or less and, most particularly, with a molecular weight of 500 Daltons or less.

As the recruiting element binds to the VLP-forming polypeptide, and there typically is more than one VLP-forming polypeptide in a virus-like particle, there can be more than one fusion construct in the VLP. Typically, the fusion constructs comprising two small molecules are identical in a VLP (so that the same prey proteins can be identified), but this need not be the case.

The fusion construct contains a small molecule acting as recruiting element, and a small molecule acting as bait, wherein both molecules are covalently connected. The nature and the length of the covalent linker used in the fusion construct are not vital to the disclosure (as long as they do not interfere with incorporation in the VLP). Particularly envisaged herein is the use of polyethyleneglycol (PEG) as a covalent linker between the molecules in the fusion construct.

The small molecule recruiting element as used here is a compound that recruits, directly or indirectly, the small molecule bait together with its physiological binding partners into VLPs. Typically, this is done by binding of the VLP-forming polypeptide. In other words, the small molecule recruiting element has an affinity for the VLP-forming polypeptide, and is able to interact with (or bind to) the VLP-forming polypeptide.

Since it is particularly envisaged that the VLP-forming polypeptide is a fusion protein, the small molecule recruiting element does not need to have an affinity for a native VLP-forming polypeptide, but can have affinity for a different protein. This allows greater flexibility in the choice of recruiting element and VLP-forming polypeptide. According to these embodiments, the fusion protein partner of the VLP-forming polypeptide interacts with the recruiting element of the small molecule fusion.

Many small molecules that have affinity for a given protein are known to the skilled person, and the nature of the binding pair (recruiting element/fusion protein partner of the VLP-forming polypeptide) is not essential, on condition that the fusion protein still effectively forms VLPs. According to particular embodiments, the small molecule recruiting element is selected from the group consisting of methotrexate (MTX) and trimethoprim (TMP). According to a specific embodiment, the small molecule recruiting element is not MTX. According to a specific embodiment, the fusion construct comprising two small molecules is not an MTX-based fusion construct.

The other small molecule of the fusion construct, the bait molecule, is used to attract an interacting polypeptide. The binding partner of the bait molecule may be known (e.g., to confirm an interaction, for instance for modified proteins) or unknown (e.g., in identifying targets of a given small molecule drug). According to a specific embodiment, the binding partner of the bait molecule (the prey protein) is unknown. According to a specific embodiment, the small molecule bait is known and the interacting prey protein is unknown. The interaction between the small molecule and its prey protein can be covalent or non-covalent, and can be direct or indirect. According to a specific embodiment, the interaction between the small molecule bait and the interacting prey protein is direct. According to a particular embodiment, the polypeptide bait is unknown and binds to a known small molecule bait.

According to a specific embodiment, an artificial VLP is provided, consisting of:
(a) a VLP-forming polypeptide;
(b) a fusion construct comprising two small molecules covalently linked to each other, wherein the first small molecule ("recruiting element") interacts with the VLP-forming polypeptide and the second small molecule ("bait") interacts with at least one polypeptide different from the VLP-forming polypeptide; and
(c) a polypeptide ("prey") interacting with the second small molecule ("bait") of (b).

According to a very specific embodiment, the small molecule bait is not FK506. Besides the small molecule fusion construct and the interacting polypeptide, the virus-like particle may comprise other compounds, recruited to the small molecule-protein complex, wherein all the compounds together form one complex. In a particular embodiment, the VLP as described above entraps two molecular interactions, i.e., the molecular interaction between the VLP-forming polypeptide and the fusion construct comprising two small molecules and the molecular interaction between the fusion construct and the prey polypeptide. In a very specific embodiment, the VLP as described above does not entrap three molecular interactions, i.e., not more than the two molecular interactions described above. In a very specific embodiment, the molecular interactions are non-covalent interactions. In a specific embodiment, the molecular interactions do not trigger posttranslational modifications, such as, but not limited to, phosphorylations. According to some embodiments, the prey polypeptide interacting with the small molecule bait is a polypeptide isolated in physiological conditions, i.e., a naturally occurring polypeptide, or parts thereof, and not a fusion protein. According to a particular embodiment, the prey polypeptide is a fusion protein, wherein an unknown prey polypeptide is fused to a known (fusion partner) protein and the fusion partner protein does not act as bait. According to some embodiments, the interacting polypeptide is the sole interaction partner of the bait small molecule of the fusion construct. However, it is also possible that more than one single protein is included in one VLP (e.g., if the fusion construct interacts with more than one single protein), wherein each prey protein interacts directly with the bait. According to some embodiments, complexes of two or more different proteins are included in one VLP, wherein the different proteins interact directly and/or indirectly with the bait.

The prey protein can be an endogenous protein, can be provided by transfection of expression plasmids or by RNA transfection in the cell producing the VLPs, or can be added directly as a recombinant protein.

Of note, one bait small molecule may be able to bind to several prey polypeptides. Thus, when referring to a polypeptide ("prey") interacting with the second small molecule in the VLP, it is explicitly meant that "a" is one or more. Indeed, there can be different polypeptides in the same VLP, even if only one type of fusion construct is used.

The VLP-forming polypeptide (or typically, a multitude thereof) forms a viral structure, consisting of a hollow particle, in which the small molecule fusion construct and the interacting (prey) polypeptides are trapped. In particular embodiments, the small molecule fusion is anchored to the viral structure, ensuring the capturing of the complex formed by the small molecule fusion and the prey polypeptide into the inside of the virus-like particle. Preferably, the anchoring of the small molecule fusion is direct to the VLP-forming polypeptide, and does not comprise any independent linker molecule. An "independent linker molecule," according to the this disclosure, is a molecule that binds non-covalently to the viral particle-forming protein at one hand, and to a fusion protein at the other hand.

The VLPs provided herein are particularly useful for the detection of small molecule-protein interactions, particularly in native and/or physiological conditions. Accordingly, in another aspect of the disclosure, the use of an artificial virus-like particle, as described herein, is provided for the detection of small molecule-protein interactions.

Still another aspect of the disclosure is a method for detecting small molecule-protein interactions, comprising (1) expressing a VLP-forming polypeptide in a cell; (2) recruiting a fusion construct comprising two small molecules covalently linked to each other, wherein the first small molecule interacts with the VLP-forming polypeptide and the second small molecule interacts with at least one polypeptide different from the VLP-forming polypeptide, to the VLP-forming polypeptide; (3) allowing a polypeptide to interact with the second small molecule of (2) to the fusion construct; (4) isolating the VLPs; and (5) analyzing the entrapped complex. In a specific embodiment, the method as described above detects novel small molecule-protein interactions, i.e., interactions of small molecules and proteins that have not been described before. In a particular embodiment, the method as described above detects interactions between a known small molecule bait and an unknown protein. the unknown protein can be provided by, e.g., but not limited to, a protein library that can be expressed from, but not limited to, a cDNA library. In a specific embodiment, the protein library provides more than one potential binding partner for the small molecule bait. In a specific embodiment, the protein library provides more than two potential binding partners for the small molecule bait. In a specific embodiment, the protein library provides more than ten potential binding partners for the small molecule bait. In a specific embodiment, the protein library provides more than $10^2$ potential binding partners for the small molecule bait. In a specific embodiment, the protein library provides more than $10^3$ potential binding partners for the small molecule bait. In a specific embodiment, the protein library provides more than $10^4$ potential binding partners for the small molecule bait. In a specific embodiment, the protein library provides more than $10^5$ potential binding partners for the small molecule bait. In a specific embodiment, the protein library provides more than $10^6$ potential binding partners for the small molecule bait. In a particular embodiment, a single small molecule bait is used to screen protein libraries. In a particular embodiment, a single small molecule bait is used to screen cDNA libraries. In a particular embodiment, a single small molecule bait is used to screen ORF libraries.

Preferably, the cell is a mammalian cell.

Steps 1-3 result in the generation of a VLP with a complex entrapped therein. The order of steps 1-3 can differ. For instance, the polypeptide interacting with the second small molecule may first bind to the fusion construct prior to interaction of the first small molecule of the fusion construct with the VLP-forming polypeptide.

Isolating the VLPs can, e.g., be done by means of a purification tag. A tagged version (e.g., FLAG-tag) of the vesicular stomatitis virus glycoprotein (VSV-G), a transmembrane protein typically used for pseudotyping lentiviral vectors, can be expressed in the producer cells to allow a simple one-step purification. Isolating is then typically done by affinity chromatography or a similar method using an antibody directed against the tag (e.g., M2 anti-FLAG antibody). Antibodies directed against VSV-G itself or other molecules present on the surface can be used to enrich VLPs. Other methods of VLP enrichment include ultracentrifugation of supernatant containing VLPs, gradient centrifugation of supernatant containing VLPs or precipitation of the VLPs from supernatant using precipitating agents. These methods require a centrifugation step to pellet VLPs. These pellets can be re-dissolved and processed for analysis. Filtration kits to enrich and purify particles are also available.

Typically, analysis of the entrapped complex will entail identification of the polypeptide interacting with the second small molecule. Particularly, the analysis of the entrapped molecular complex is an MS-based analysis. If a particular polypeptide is expected, a western blot analysis can be performed to confirm the presence of the polypeptide in the particles. It is clear for the person skilled in the art that molecular interactions of any nature can be detected with the method.

It is to be understood that although particular embodiments, specific configurations as well as materials and/or molecules, have been discussed herein for cells and methods according to this disclosure, various changes or modifications in form and detail may be made without departing from the scope and spirit of this disclosure. The following examples are provided to better illustrate particular embodiments, and they should not be considered limiting the application. The application is limited only by the claims.

EXAMPLES

Materials and Methods
Generation of Plasmids

The p55 GAG fusion constructs were generated by PCR amplification of the p55 GAG coding sequence using primer 1 (5'-CTCTAAAAGCTGCGGGGCCCGC TAGCGCCAC-CATGGGTGCGAGAGCGTCAG-3' (SEQ ID NO:1)) and primer 2 (5'-TGTATTCGGTGAATTCT-GAGCTCGTCGACCCGCCTTGTGACGAGGGGTCGC TGC-3' (SEQ ID NO:2)) from the pCMV-dR8.74 packaging construct (Addgene) and by subsequent In-Fusion™ reaction (Clontech) in pMG1-Ras, a Ras expression vector used in the MAPPIT system (Eyckerman et al., 2001), resulting in a p55 GAG-RAS under control of the strong SRalpha promoter (pMET7-GAG-Ras). The pMD2.G pseudotyping vector, expressing VSV-G under control of a CMV promoter, was kindly provided by Didier Trono (EPFL, Lausanne, Switzerland). The pcDNA3-FLAG-VSV-G and pcDNA3-Etag-VSV-G were cloned by introducing the respective epitope coding sequences in a permissive site in the extracellular part of VSV-G. The coding sequence for the *E. coli* dihydrofolate reductase (eDHFR) was transferred into the pMET7-GAG plasmid from previous constructs (Risseeuw et al., 2013). Synthesis of the small molecule fusions was described before (Risseeuw et al., 2013; Lievens et al., 2014).

Production and Analysis of VLPs

For mass spectrometry, $10^7$ HEK293T cells were seeded in five flasks (75 cm$^2$) and transfected the next day with a total of 15 µg DNA per flask using polyethylene imine reagent. The following DNA quantities were used per flask: 7.5 µg of GAG-eDHFR, 5.4 µg of mock vector and 2.1 µg of a 50/50 mix of pMD2.G and pcDNA3-FLAG-VSV-G. The small molecule fusions were added immediately after transfection to the producing cells at a concentration of 1 µM. The same dilution of dimethyl sulfoxide (DMSO) was added in control experiments to control the effect of this chemical on the cells. The cellular supernatant was harvested after 32 hours and was centrifuged for 3 minutes at 450×g to remove cellular debris. The cleared supernatant was then filtered using 0.45 µm filters (Millipore). A total of 100 µl MyOne™ Streptavidin T1 beads (Life Technologies) pre-loaded with 10 µg ANTI-FLAG® BioM2-Biotin antibody (Sigma-Aldrich®) was used to bind the tagged particles. Particles were allowed to bind for 2 hours by end-over-end rotation. The total supernatant was processed in three consecutive binding steps. Bead-particle complexes were washed once with washing buffer (TWB: 20 mM Tris-HCl pH 7.5, 150 mM NaCl) and were then eluted with FLAG peptide (200 µg/ml in TWB) and lysed by addition of SDS to a final concentration of 0.1%. After 5 minutes, SDS was removed using HiPPR Detergent Removal Spin Columns (Pierce, Thermo Scientific) followed by boiling and overnight digestion with 0.5 µg sequence-grade trypsin (Promega). After acidification (0.1% TFA final), the peptides were separated by nano-LC and directly analyzed with a Q Exactive instrument (Thermo Scientific). Searches were performed using the MASCOT algorithm (Version 2.4.1. Matrix Science) at 99% confidence against human and bovine SWISSPROT accessions (Release 2013_02) complemented with HIV-1, EGFP, VSV-G and FLAG-VSV-G protein sequences.

Example 1: Viral Trapping of Simvastatin Binders

To screen for simvastatin binders, cells were transfected with the GAG-eDHFR construct and then treated immediately after transfection with the MTX-PEG6-simvastatin molecule. A total of five biological repeats were performed together with four DMSO control experiments. The list of candidate interactors was obtained after removal of all proteins (including proteins identified with a single peptide) that were found in 19 control samples, the four DMSO samples and the other small molecule samples (e.g., the protein list of the five simvastatin samples was challenged against a total of 29 samples). The control samples are a number of successful Virotrap experiments using unrelated proteins to generate a list of proteins that can be considered background proteins, and that can be subtracted from the protein list obtained for the actual samples.

For each small molecule condition, two lists of proteins (annotated by their gene name) were reported. The left part of the tables ("All proteins") contains all unique protein identifications (thus also proteins identified with a single peptide) obtained after removal of the background proteins. The right part of the tables ("Proteins identified with >1 peptide") contains only the proteins identified with high confidence (at least two modified peptide identifications for each protein). Some recurrent proteins that were identified in multiple experiments with a single peptide are removed from this list (e.g., PYGM identified with low confidence in two repeat experiments).

For simvastatin, 3-hydroxy-3-methylglutaryl coenzyme A reductase (gene name: HMGCR), the primary target for the statin family of molecules, was identified in all five biological repeat experiments. In addition, squalene epoxidase (SQLE) was identified with at least two peptides in three experiments. This enzyme is an important downstream component of the sterol biosynthesis pathway, and may interact directly with HMGCR. UBIAD1, a known interaction partner of the HMGCR protein (Nickerson et al., 2013) was identified in one experiment with at least two peptides. SARM1 may be a novel target protein for simvastatin.

TABLE 1

Proteins identified with the MTX-PEG6-simvastatin small molecule fusion construct. All protein identifications (including single peptide identifications) or identified proteins with at least two peptides are shown with their recurrent identification in five biological replicates.

| Gene name | Recurrence (x/5) |
|---|---|
| All proteins (incl. low confidence identifications) | |
| HMGCR | 5 |
| SQLE | 4 |
| SARM1 | 3 |
| PYGM | 2 |
| AKT3 | 1 |
| ATP6V0C | 1 |
| CNPY2 | 1 |

TABLE 1-continued

Proteins identified with the MTX-PEG6-simvastatin small molecule fusion construct. All protein identifications (including single peptide identifications) or identified proteins with at least two peptides are shown with their recurrent identification in five biological replicates.

| Gene name | Recurrence (x/5) |
|---|---|
| CTU1 | 1 |
| DBI | 1 |
| DDTL | 1 |
| EIF1AY | 1 |
| FABP1 | 1 |
| FHL1 | 1 |
| GALNT1 | 1 |
| GINS1 | 1 |
| KIAA0319L | 1 |
| KRT6B | 1 |
| LAMTOR5 | 1 |
| LNPEP | 1 |
| LOC512271 | 1 |
| LOC524129 | 1 |
| MOXD1 | 1 |
| PDIA4 | 1 |
| PRKCSH | 1 |
| RAB4A | 1 |
| RBP4 | 1 |
| SBDS | 1 |
| SH3GL2 | 1 |
| SLC17A1 | 1 |
| SLC46A1 | 1 |
| TMED5 | 1 |
| TMED9 | 1 |
| UBIAD1 | 1 |
| VAMP4 | 1 |
| VPS37D | 1 |
| Proteins identified with >1 peptide (high confidence) | |
| HMGCR | 5 |
| SARM1 | 3 |
| SQLE | 3 |
| CTU1 | 1 |
| KIAA0319L | 1 |
| KRT6B | 1 |
| PDIA4 | 1 |
| UBIAD1 | 1 |

Example 2: Viral Trapping of Tamoxifen Binders

For tamoxifen, four biological repeats were performed where the cells were treated with MTX-PEG6-tamoxifen after transfection. The obtained protein lists after viral trapping and MS analysis were challenged with protein lists coming from the four DMSO controls, the 19 control experiments and the lists obtained for the MTX-PEG6-simvastatin and MTX-PEG6-reversine (see below) for a total of 30 samples.

The results were presented similarly as for the simvastatin example (see Example 1) with a table containing gene name identifiers and recurrence of detection in four experiments, for both high confidence and low confidence identifications (see Table 2).

TABLE 2

Proteins identified with the MTX-PEG6-tamoxifen small molecule fusion construct. All protein identifications (including single peptide identifications) or identified proteins with at least two peptides are shown with their recurrent identification in four biological replicates.

| Gene name | Recurrence (x/4) |
|---|---|
| All proteins (incl. low confidence identifications) | |
| HSD17B4 | 4 |
| REEP6 | 4 |
| SSNA1 | 4 |
| RNF5 | 3 |
| TBL2 | 3 |
| DCAKD | 2 |
| EI24 | 2 |
| REEP4 | 2 |
| SEC61G | 2 |
| ATL2 | 1 |
| C28H10ORF35 | 1 |
| CALU | 1 |
| CGN1 | 1 |
| CYP51A1 | 1 |
| DNAJB12 | 1 |
| ECE1 | 1 |
| ENPP4 | 1 |
| EPHX1 | 1 |
| ESYT1 | 1 |
| ESYT2 | 1 |
| FAM62A | 1 |
| GRAMD4 | 1 |
| HSD17B12 | 1 |
| ILVBL | 1 |
| ITPRIPL1 | 1 |
| LRRC59 | 1 |
| MDH2 | 1 |
| MINK1 | 1 |
| NCS1 | 1 |
| PCSK5 | 1 |
| PRAF2 | 1 |
| PRSS3 | 1 |
| PTPLAD1 | 1 |
| RTN3 | 1 |
| RTN4 | 1 |
| SEC61B | 1 |
| SEMA4G | 1 |
| SREBF2 | 1 |
| SSR3 | 1 |
| TAOK2 | 1 |
| TMPRSS13 | 1 |
| UBQLN2 | 1 |
| VAPA | 1 |
| WDR36 | 1 |
| ZMPSTE24 | 1 |
| Proteins identified with >1 peptide (high confidence) | |
| HSD17B4 | 4 |
| REEP6 | 3 |
| REEP4 | 2 |
| SSNA1 | 2 |
| TBL2 | 2 |
| ECE1 | 1 |
| ESYT1 | 1 |
| ESYT2 | 1 |
| FAM62A | 1 |
| MDH2 | 1 |
| RTN4 | 1 |
| SEC61G | 1 |
| UBQLN2 | 1 |
| VAPA | 1 |

The interaction between tamoxifen and HSD17B4 was confirmed using a binary MASPIT assay (see Example 4).

Example 3: Viral Trapping of Reversine Binders

For reversine, two experiments were formed where cells were transfected with the GAG-eDHFR construct and then treated after transfection with MTX-PEG6-reversine during VLP production. After purification and proteomic analysis, the obtained lists were challenged with the combined proteome list of the four DMSO and 19 unrelated control experiments, and of the MTX-PEG6-simvastatin and MTX-PEG6-tamoxifen lists.

TABLE 3

Proteins identified with the MTX-PEG6-reversine small molecule fusion construct. All protein identifications (including single peptide identifications) or identified proteins with at least two peptides are shown with their recurrent identification in two biological replicates.

| Gene name | Recurrence (x/2) |
|---|---|
| All proteins (incl. low confidence identifications) | |
| IGF1R | 2 |
| INSR | 2 |
| NQO2 | 2 |
| APMAP | 1 |
| BZW1 | 1 |
| CAMKV | 1 |
| CTNNA2 | 1 |
| DYNC2H1 | 1 |
| FKBP3 | 1 |
| GAK | 1 |
| GEMIN5 | 1 |
| HTRA3 | 1 |
| LMAN1 | 1 |
| MBTPS1 | 1 |
| MFI2 | 1 |
| MST1R | 1 |
| MYO1D | 1 |
| NEK2 | 1 |
| NT5C | 1 |
| PPM1L | 1 |
| RCL | 1 |
| RPS6KA1 | 1 |
| TMEM30A | 1 |
| TMEM9 | 1 |
| TMX1 | 1 |
| USP7 | 1 |
| YIPF5 | 1 |
| ZNF827 | 1 |
| Proteins identified with >1 peptide (high confidence) | |
| IGF1R | 2 |
| INSR | 2 |
| GEMIN5 | 1 |
| NQO2 | 1 |
| RCL | 1 |

Example 4: Confirmation of the Interaction Between Tamoxifen and HSD17B4 Using a MASPIT Assay The binding of HSD17B4 to tamoxifen was further confirmed using the MASPIT technology. The binary MASPIT assay was essentially performed as described before (Risseeuw et al., 2013). Briefly, HEK293T cells were seeded in black tissue-culture treated 96-well plates at 10.000 cells/well in 100 µl culture medium (DMEM supplemented with 10% fetal calf serum), and grown at 37° C., 8% CO$_2$. Twenty-four hours later cells were transfected with a combination of the pCLG-eDHFR plasmid (Risseeuw et al., 2013), the pMG1-HSD17B4 construct and the pXP2d2-rPAP1-luciferase reporter (Caligiuri et al., 2006). The pMG1-HSD17B4 construct was generated by Gateway transfer of the full size HSD17B4 ORF, obtained as an entry clone in the hORFeome collection, into the Gateway compatible pMG1 prey destination vector as described earlier (Lievens et al., 2009). Twenty-four hours after transfection, cells were either left unstimulated or treated with 100 ng/ml leptin, with or without addition of MTX-PEG6-tamoxifen. Another 24 hours later, luciferase activity was assayed using the Luciferase Assay System kit (Promega).

Figure 4:
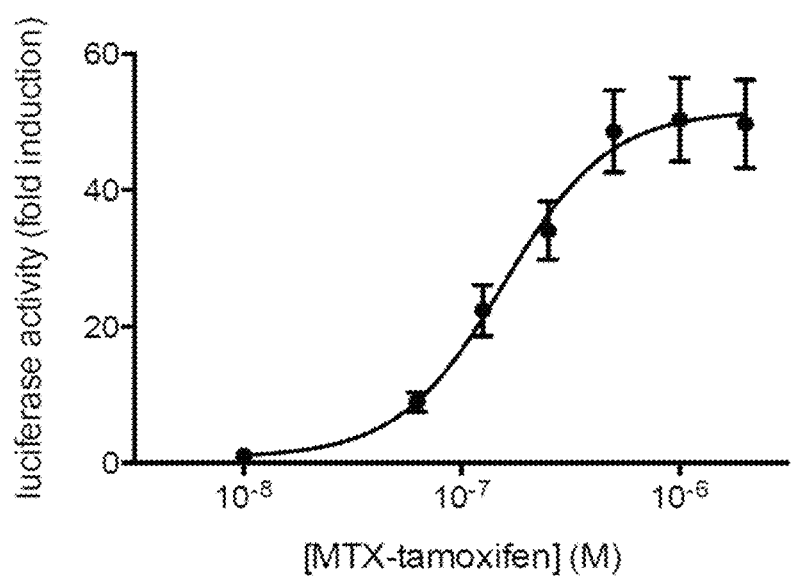
FIG. 4: Dose-response curve of the MASPIT signal obtained for the interaction between the MTX-PEG6-tamoxifen molecule and HSD17B4. Luciferase activity is expressed as fold induction compared to control samples treated without the small molecule fusion. Error bars represent the standard deviation of technical triplicates.

As shown in FIG. 4, the binary MASPIT assay showed increased luciferase activity in a dose-dependent manner upon addition of MTX-PEG6-tamoxifen, confirming the interaction of tamoxifen with HSD17B4.

REFERENCES

Bantscheff, M., Eberhard, D., Abraham, Y., Bastuck, S., Boesche, M., Hobson, S., Mathieson, T., Perrin, J., Raida, M., Rau, C., Reader, V., Sweetman, G., Bauer, A., Bouwmeester, T., Hopf, C., Kruse, U., Neubauer, G., Ramsden, N., Rick, J., Kuster, B. and Drewes, G. (2007). Quantitative chemical proteomics reveals mechanisms of action of clinical ABL kinase inhibitors. *Nat. Biotechnol.* 25:1035-44.

Bardwell V. J. and Wickens, M. (1990). Purification of RNA and RNA-protein complexes by an R17 coat protein affinity method. *Nucl. Acids Res.* 18:6587-6594.

Caligiuri, M., Molz, L., Liu, Q., Kaplan, F., Xu, J. P., Majeti, J. Z., Ramos-Kelsey, R., Murthi, K., Lievens, S., Tavernier, J., et al. (2006). MASPIT: three-hybrid trap for quantitative proteome fingerprinting of small molecule-protein interactions in mammalian cells. *Chem. Biol.* 13:711-722.

Eyckerman, S., Verhee, A., der Heyden J. V., Lemmens, I., Ostade, X. V., Vandekerckhove, J. and Tavernier, J. (2001). Design and application of a cytokine-receptor-based interaction trap. *Nat. Cell Biol.* 3:1114-9.

Fields, S. and Song, 0. (1989). A novel genetic system to detect protein-protein interactions. *Nature* 340:245-246.

Gavin, A. C., Bosche, M., Krause, R., Grandi, P., Marzioch, M., Bauer, A., Schultz, J., Rick, J. M., Michon, A. M., Cruciat, C. M., et al. (2002). Functional organization of the yeast proteome by systematic analysis of protein complexes. *Nature* 415:141-147.

Gingras, A. C., Gstaiger, M., Raught, B. and Aebersold, R. (2007). Analysis of protein complexes using mass spectrometry. *Nat. Rev. Mol. Cell Biol.* 8:645-654.

Lievens, S., Gerlo, S., Lemmens, I., De Clercq, D. J., Risseeuw, M. D., Vanderroost, N., De Smet, A. S., Ruyssinck, E., Chevet, E., Van Calenbergh, S. and Tavernier, J. (2014). Kinase Substrate Sensor (KISS), a Mammalian In Situ Protein Interaction Sensor. *Mol. Cell Proteomics* 13:3332-42.

Lievens, S., Vanderroost, N., Van der Heyden, J., Gesellchen, V., Vidal, M. and Tavernier, J. (2009). Array MAPPIT: high-throughput interactome analysis in mammalian cells. *J. Proteome Res.* 8:877-86.

Malovannaya, A., Lanz, R. B., Jung, S. Y., Bulynko, Y., Le, N. T., Chan, D. W., Ding, C., Shi, Y., Yucer, N., Krenciute, G., et al. (2011). Analysis of the human endogenous coregulator complexome. *Cell* 145:787-799.

Nickerson, M. L., Bosley, A. D., Weiss, J. S., Kostiha, B. N., Hirota, Y., Brandt, W., Esposito, D., Kinoshita, S., Wessjohann, L., Morham, S. G., Andresson, T., Kruth, H. S., Okano, T. and Dean, M (2013). The UBIAD1 prenyltransferase links menaquinone-4 synthesis to cholesterol metabolic enzymes. *Hum. Mutat.* 34:317-29.

Ong, S. E., Schenone, M., Margolin, A. A., Li, X., Do, K., Doud, M. K., Mani, D. R., Kuai, L., Wang, X., Wood, J. L., Tolliday, N. J., Koehler, A. N., Marcaurelle, L. A., Golub, T. R., Gould, R. J., Schreiber, S. L. and Carr, S. A. (2009). Identifying the proteins to which small-molecule probes and drugs bind in cells. *Proc. Natl. Acad. Sci. U.S.A.* 106:4617-22.

Paul, F. E., Hosp, F. and Selbach, M. (2011). Analyzing protein-protein interactions by quantitative mass spectrometry. *Methods* 54:387-395.

Risseeuw, M. D., De Clercq, D. J., Lievens, S., Hillaert, U., Sinnaeve, D., Van den Broeck, F., Martins, J. C., Tavernier, J. and Van Calenbergh, S. (2013). A "clickable" MTX reagent as a practical tool for profiling small-molecule-intracellular target interactions via MASPIT. *Chem. Med. Chem.* 8:521-6.

Savitski, M. M., Reinhard, F. B., Franken, H., Werner, T., Savitski, M. F., Eberhard, D., Martinez Molina, D., Jafari, R., Dovega, R. B., Klaeger, S., Kuster, B., Nordlund, P., Bantscheff, M. and Drewes, G. Tracking cancer drugs in living cells by thermal profiling of the proteome. *Science* 346:1255784-1-10.

Walker, S. C., Scott, F. H., Srisawat, C. and Engelke, D. R. (2008). RNA affinity tags for the rapid purification and investigation of RNAs and RNA-protein complexes. *Methods Mol. Biol.* 488:23-40.

Windbichler, N. and Schroeder, R. (2006). Isolation of specific RNA-binding proteins using the streptomycin-binding RNA aptamer. *Nat. Protocols* 1:637-640.

What is claimed is:

1. A method for detecting a small molecule-protein interaction, the method comprising:
    expressing a fusion protein comprising a virus-like particle (VLP)-forming polypeptide;
    recruiting to the fusion protein a small molecule construct comprising a first and a second small molecule covalently linked to one another, wherein the first small molecule of the small molecule construct interacts with the fusion protein and the second small molecule of the small molecule construct interacts with at least one polypeptide other than the fusion protein;
    interacting the at least one polypeptide other than the fusion protein with the second small molecule of the small molecule construct;
    forming and isolating VLPs comprising the fusion protein; and
    analyzing an entrapped complex in the isolated VLP.

2. The method according to claim 1, wherein the VLPs are isolated by affinity chromatography.

3. The method according to claim 1, wherein the entrapped complex is analyzed by mass spectrometry.

4. The method according to claim 1, wherein the VLP-forming polypeptide is a fusion protein comprising a VLP-forming polypeptide and a protein recruiting the first small molecule of the small molecule construct.

5. The method according to claim 4 wherein the fusion protein comprises HIV p55 GAG protein as the VLP-forming polypeptide.

6. The method according to claim 1, wherein the polypeptide interacting with the second small molecule of the small molecule construct is a physiological binding partner of the second small molecule.

7. The method according to claim 1, wherein the first small molecule of the small molecule construct is not methotrexate.

8. The method according to claim 1, wherein the VLP-forming polypeptide further comprises a purification tag.

9. The method according to claim 6, wherein the fusion protein comprises HIV p55 GAG protein as VLP-forming polypeptide.

* * * * *

SEQUENCE LISTING

<160> NUMBER OF SEQ ID NOS: 2

<210> SEQ ID NO 1
<211> LENGTH: 51
<212> TYPE: DNA
<213> ORGANISM: Artificial Sequence
<220> FEATURE:
<223> OTHER INFORMATION: Primer

<400> SEQUENCE: 1
ctctaaaagc tgcggggccc gctagcgcca ccatgggtgc gagagcgtca g        51

<210> SEQ ID NO 2
<211> LENGTH: 54

```
<212> TYPE: DNA
<213> ORGANISM: Artificial Sequence
<220> FEATURE:
<223> OTHER INFORMATION: Primer

<400> SEQUENCE: 2
tgtattcggt gaattctgag ctcgtcgacc cgccttgtga cgaggggtcg ctgc          54
```